United States Patent
Nawasra et al.

(10) Patent No.: US 9,829,445 B2
(45) Date of Patent: Nov. 28, 2017

(54) TESTING DIFFRACTION OR DIFFUSION OF A LIGHT BEAM

(71) Applicant: Apple Inc., Cupertino, CA (US)

(72) Inventors: Jawad Nawasra, San Francisco, CA (US); Yazan Z. Alnahhas, Mountain View, CA (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 14/957,643

(22) Filed: Dec. 3, 2015

(65) Prior Publication Data
US 2017/0160209 A1 Jun. 8, 2017

(51) Int. Cl.
*G01N 21/958* (2006.01)

(52) U.S. Cl.
CPC . *G01N 21/958* (2013.01); *G01N 2201/06113* (2013.01)

(58) Field of Classification Search
CPC ....... G01B 11/00; G02B 26/105; G01T 1/185; G01T 1/2935; H01L 31/02024; H01L 31/184; G01N 21/958; G01N 2201/06113
See application file for complete search history.

(56) References Cited

U.S. PATENT DOCUMENTS

| | | | |
|---|---|---|---|
| 3,997,715 A | 12/1976 | Elliott | |
| 4,454,422 A * | 6/1984 | Persyk | G01T 1/1645 250/363.02 |
| 4,762,993 A | 8/1988 | Moses | |
| 5,481,109 A | 1/1996 | Ninomiya et al. | |
| 5,937,026 A | 8/1999 | Satoh | |
| 6,207,958 B1 * | 3/2001 | Giakos | G01T 1/185 250/374 |
| 6,429,417 B1 | 8/2002 | Street et al. | |
| 6,862,076 B2 | 3/2005 | Mulder et al. | |
| 8,669,588 B2 * | 3/2014 | Smith | H01L 31/02024 250/214.1 |
| 8,829,406 B2 | 9/2014 | Akerman et al. | |
| 2010/0308371 A1 * | 12/2010 | Bui | H01L 31/02024 257/184 |
| 2015/0145097 A1 * | 5/2015 | Basu | H01L 31/1105 257/462 |
| 2016/0265902 A1 * | 9/2016 | Nawasra | G01B 11/00 |

OTHER PUBLICATIONS

Nawasra et al., U.S. Appl. No. 15/065,904, filed Mar. 10, 2016.
Hamamatsu., "Characteristic and Use", 7 pages, Jan. 19, 2011 www.hamamatsu.com/resources/pdf/ssd/psd_techinfo_e.pdf.

* cited by examiner

*Primary Examiner* — Sang Nguyen
(74) *Attorney, Agent, or Firm* — D.Kligler IP Services Ltd.

(57) ABSTRACT

An apparatus for testing diffraction or diffusion of a light beam is provided. The apparatus includes a photosensitive semiconductor, shaped to define an aperture. At least one anode, and a plurality of cathodes, are coupled to the semiconductor. An optical element, configured to modify an angular spread of a light beam that traverses the optical element, is disposed within the aperture. A detector is configured to detect electric currents that pass between the cathodes and the anode in response to a portion of the light beam exiting the optical element and hitting the semiconductor. Other embodiments are also described.

20 Claims, 3 Drawing Sheets

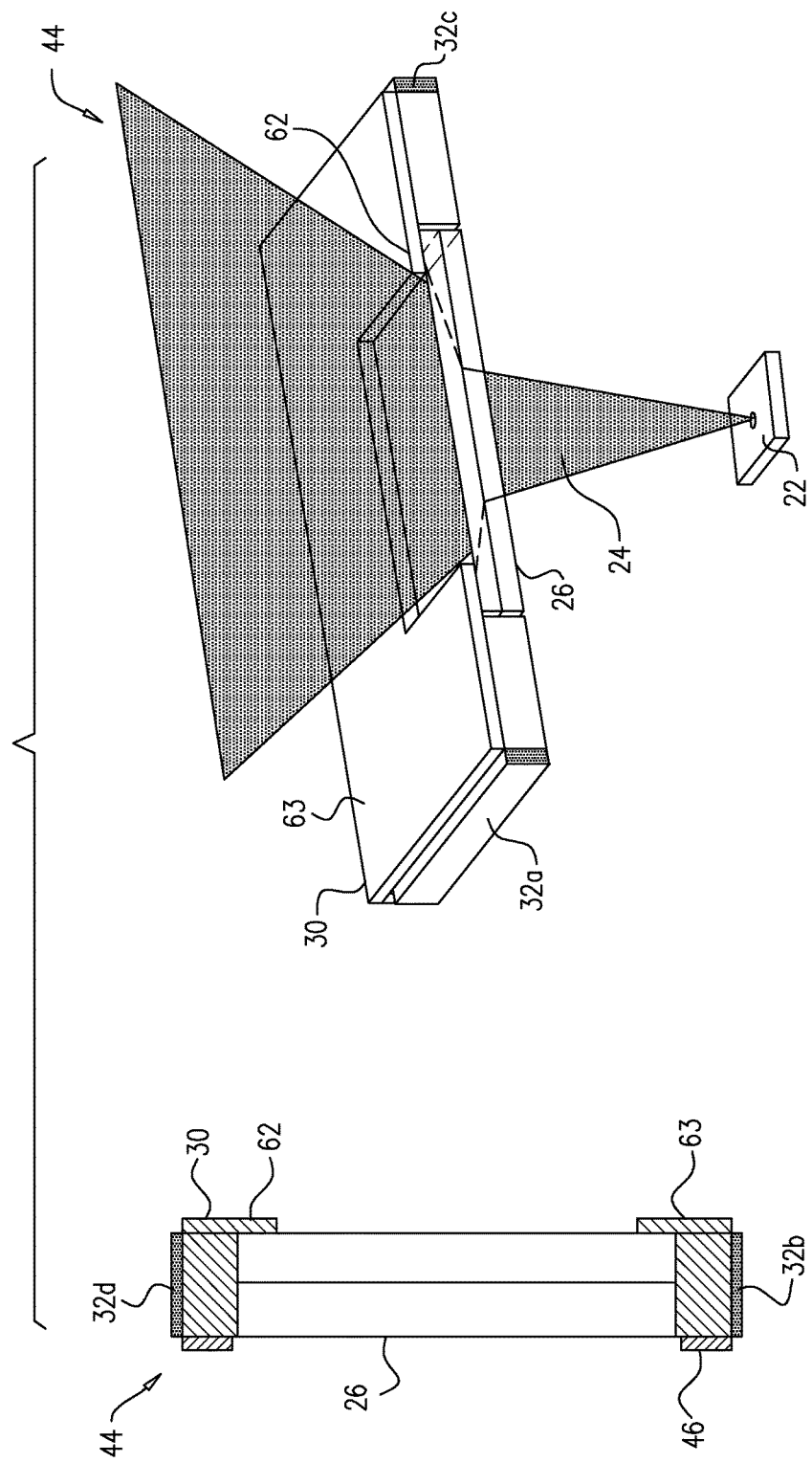

TESTING DIFFRACTION OR DIFFUSION OF A LIGHT BEAM

FIELD OF THE DISCLOSURE

Embodiments described herein relate to testing diffraction or diffusion of a light beam.

BACKGROUND

U.S. Pat. No. 8,829,406 to Akerman, whose disclosure is incorporated herein by reference, describes optical apparatus that includes a device package, with a radiation source contained in the package and configured to emit a beam of coherent radiation. A diffractive optical element (DOE) is mounted in the package so as to receive and diffract the radiation from the radiation source into a predefined pattern comprising multiple diffraction orders. An optical detector is positioned in the package so as to receive and sense an intensity of a selected diffraction order of the DOE.

U.S. Pat. No. 3,997,715 to Elliot, whose disclosure is incorporated herein by reference, describes a focus detector that includes apertured photodetectors which intercept a radiant beam. Changes in focus differentially affect the amount of radiation impinging on the detectors resulting in corresponding changes in their signal output. A videodisc system employing the detector moves a focusing lens to compensate for variations in the position of a target videodisc, so that a scanning beam is always accurately transmitted to a detector. A difference circuit connected to two photodetectors generates a driving signal to energize a lens-moving motor for shifting the focusing lens toward or away from the videodisc.

U.S. Pat. No. 6,862,076 to Mulder, whose disclosure is incorporated herein by reference, presents a system and method for determining the stray radiation condition of a projection system. The invention includes providing a detector with a detector aperture coincident with the image plane of the projection system, measuring a reference parameter in accordance with the projection beam intensity, measuring a stray radiation parameter of an image of an isolated feature and calculating a coefficient representative of the stray radiation condition of the projection system based on the measured stray radiation parameter and the reference parameter. The extent of the detector aperture fits within the extent of a notional shape, which is defined by first scaling down the shape of the feature and subsequently displacing each line element constituting the edge of the scaled down shape, parallel to itself, over a distance of at least lambda/NA in a direction perpendicular to that line element.

U.S. Pat. No. 4,762,993 to Moses, whose disclosure is incorporated herein by reference, describes a method and apparatus for sensing the deviation of a neutral particle beam from a predetermined direction. The neutral particle beam is derived from a composite particle beam having residual charged particles with substantially the same directional characteristics as the neutral particles making up the neutral particle beam. A deflection magnet deflects at least a portion of the charged particles from the composite particle beam a known amount toward a detector array including apertures for forming a plurality of charged particle beamlets. Deviation of the charged particle beamlet is determined as an indication of the direction of the neutral particle beam relative to the predetermined direction. A similar measurement of neutral particles around the periphery of the neutral beam provides deviation data of the neutral beam which, when correlated with the data of the charged particle beam, provide an instantaneous transfer characteristic of the magnetic deflection system.

U.S. Pat. No. 5,481,109 to Ninomiya, whose disclosure is incorporated herein by reference, describes a surface analysis method and an apparatus for carrying out the same in which the method involves the detection of fluorescence X-rays emitted from the surface of a sample in response to a finely focused electron beam irradiated thereto, whereby residues on the sample surface are analyzed qualitatively and quantitatively. An electron beam (1) is irradiated through a hole (9) at the center of an X-ray detector (8) into a fine hole (h) on the surface of a sample (2). In response, fluorescence X-rays are emitted from inside the fine hole (h) and are detected by an annular X-ray detector (8) having an energy analysis function near the axis of the electron beam (1) (preferably within 20 degrees with respect to the center axis of the electron beam). This arrangement allows the fluorescence X-rays from the fine hole (h) to reach the X-ray detector (8) without being absorbed by the substance of the material. That in turn ensures qualitative and quantitative analysis of high accuracy about residues in fine holes of large aspect ratios. Since the method is of non-destructive nature, the analyzed sample may be placed unscathed back into the fabrication process.

U.S. Pat. No. 5,937,026 to Satoh, whose disclosure is incorporated herein by reference, provides a structure wherein a detector for measuring the fluorescent X-rays is made into a thin and hollow cylindrical type configuration and this detector is fitted onto the vicinity of an end on the sample side of the X-ray capillary tube for decreasing primary X-rays to a thin flux.

SUMMARY OF THE DISCLOSURE

There is provided, in accordance with some embodiments described herein, an apparatus for testing diffraction or diffusion of a light beam. The apparatus includes a photosensitive semiconductor, shaped to define an aperture. At least one anode, and a plurality of cathodes, are coupled to the semiconductor. An optical element, configured to modify an angular spread of a light beam that traverses the optical element, is disposed within the aperture. A detector is configured to detect electric currents that pass between the cathodes and the anode in response to a portion of the light beam exiting the optical element and hitting the semiconductor.

In some embodiments, the optical element is selected from the group consisting of: a diffractive optical element (DOE), and a diffuser.

In some embodiments, the semiconductor is shaped to define a rectangular front face and a rectangular rear face, the aperture passing through the semiconductor from the front face to the rear face.

In some embodiments, the semiconductor is further shaped to define four outward-facing side faces between the front face and the rear face, and the cathodes include four cathodes, each of which is coupled to a respective one of the outward-facing side faces.

In some embodiments, the semiconductor includes silicon.

In some embodiments, a perimeter of the optical element is in contact with a perimeter of the aperture.

In some embodiments, the apparatus further includes a processor configured to:
compute a quantity that is based on respective magnitudes of one or more of the detected electric currents, compare the quantity to a baseline quantity, and
generate an output in response thereto.

In some embodiments, the processor is further configured to, in response to comparing the quantity to the baseline quantity, identify an abnormal power level of the light beam.

In some embodiments, the optical element is a diffractive optical element (DOE), and the processor is further configured to, in response to comparing the quantity to the baseline quantity, identify an abnormal diffraction pattern of the DOE.

In some embodiments, the apparatus further includes a light source configured to direct the light beam through the optical element.

In some embodiments, the apparatus further includes a processor configured to, in response to the detected electric currents, control the light source.

In some embodiments, the optical element is shaped to define (i) a front face at a front opening of the aperture, and (ii) a rear face at a rear opening of the aperture, and the semiconductor partially covers the rear face of the optical element.

In some embodiments, the semiconductor covers between 10% and 40% of an area of the rear face of the optical element.

In some embodiments, the semiconductor is shaped to define a plurality of faces having respective perimeters, each perimeter of which is less than 80 mm.

In some embodiments,
the semiconductor is shaped to define a plurality of faces having respective semiconductor-face perimeters,
the optical element is shaped to define a plurality of faces having respective optical-element-face perimeters, and
a ratio of a largest one of the semiconductor-face perimeters to a largest one of the optical-element-face perimeters is less than nine.

There is further provided, in accordance with some embodiments described herein, a method for testing diffraction or diffusion of a light beam. A photosensitive semiconductor shaped to define an aperture is provided, at least one anode, and a plurality of cathodes, being coupled to the semiconductor, and an optical element, configured to modify an angular spread of a light beam that traverses the optical element, being disposed within the aperture. Electric currents that pass between the cathodes and the anode in response to a portion of the light beam exiting the optical element and hitting the semiconductor are detected. An output is generated in response to the detected electric currents.

In some embodiments, the method further includes:
computing a quantity that is based on respective magnitudes of one or more of the detected electric currents; and
comparing the quantity to a baseline quantity,
and generating the output includes generating the output in response to the comparing.

In some embodiments, the quantity is a total magnitude of the electric currents.

In some embodiments, the quantity is based on a difference between two of the magnitudes.

In some embodiments, the quantity is based on a ratio between two of the magnitudes.

In some embodiments, the method further includes, using a light source, directing the light beam through the optical element.

In some embodiments, the output controls the light source.

In some embodiments, the optical element is shaped to define (i) a front face at a front opening of the aperture, (ii) a rear face at a rear opening of the aperture, and (iii) one or more side faces, and at least part of the portion of the light beam that hits the semiconductor exits from at least one of the side faces of the optical element.

In some embodiments, part of the portion of the light beam that hits the semiconductor exits from the rear face of the optical element.

There is further provided, in accordance with some embodiments described herein, a method for testing diffraction or diffusion of a light beam. By directing a light beam through a front face of an optical element, and without deflecting any portion of the light beam, a portion of the light beam is caused to pass through at least one side face of the optical element and hit a photosensitive semiconductor. Electric currents that are caused by the portion of the light beam hitting the semiconductor are detected, and an output is generated in response thereto.

In some embodiments, the portion of the light beam includes an internally scattered portion of the light beam.

In some embodiments, the optical element is a diffractive optical element (DOE), and the portion of the light beam includes a portion of the light beam that is diffracted by the DOE.

The present disclosure will be more fully understood from the following detailed description of embodiments thereof, taken together with the drawings, in which:

BRIEF DESCRIPTION OF THE DRAWINGS

FIGS. 2-3 are schematic illustrations of apparatus for testing diffraction of a light beam, in accordance with some embodiments described herein.

DETAILED DESCRIPTION OF EMBODIMENTS

Overview

Figure 1:
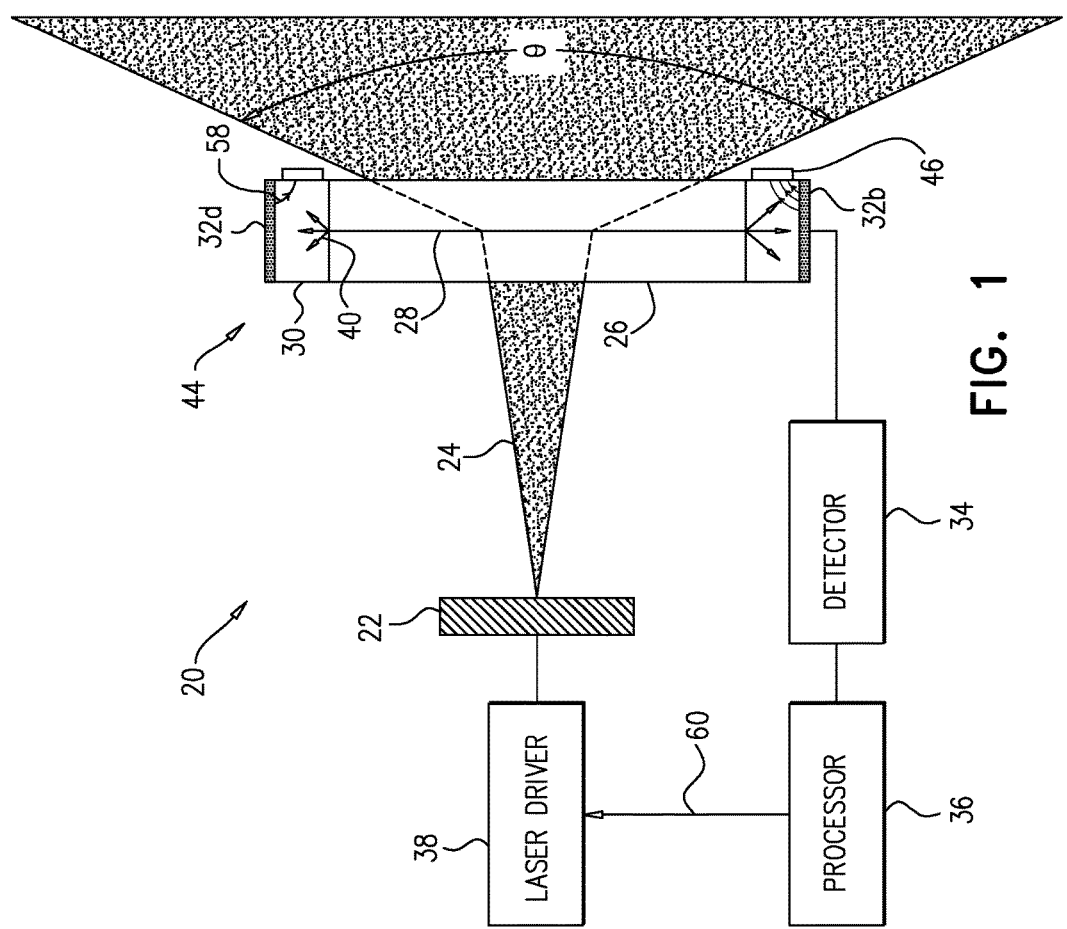
FIG. 1 is a schematic illustration of a system for testing diffraction of a light beam, in accordance with some embodiments described herein.

The term "light," as used in the context of the present description and in the claims, refers to optical radiation in any of the visible, infrared, and ultraviolet ranges.

In some applications, an optical element such as a diffractive optical element (DOE) or diffuser is used to expand (i.e., increase the angular spread of) a light beam. For example:

(i) Optical 3D mapping is the process of generating a 3D profile of the surface of an object by processing light reflected from the object. This sort of 3D profile is also referred to as a 3D map, 3D image, depth map, or depth image, and 3D mapping is also referred to as depth mapping. Typically, an optical apparatus that includes a DOE is used for depth mapping. The DOE increases the angular spread of a light beam, by generating multiple orders of diffraction of the light beam. The orders of diffraction are reflected from the surface of the object at multiple points, the reflected light from each of the multiple points is detected, and the reflected light is used to compute a depth map of the surface. Such depth mapping may be applied, for example, to user interfaces that are based on gesture recognition.

(ii) In some imaging applications, diffuse illumination is provided, by using an optical apparatus that includes a diffuser. The diffuser increases the angular spread of the light beam by diffusing the light beam.

In such applications, if the optical element does not properly expand the light beam, and/or if the intensity of the light beam is too low or too high, the depth-mapping or illumination might not be effective, and/or portions of the optical apparatus through which the light beam passes may be damaged. Hence, it is important to continually test that the optical element and the light source are working properly. Embodiments described herein provide apparatus and methods for such testing, within the context of any relevant application.

Although the present description and figures relate mainly to an optical apparatus that includes a DOE, it is noted that the scope of embodiments described herein includes any relevant type of optical element, such as, for example, a diffractive or refractive diffuser. Moreover, although the present description and figures relate mainly to applications in which a light beam is expanded, it is noted that apparatus and techniques described herein may also be applied to applications in which the angular spread of a light beam is modified in any other way, e.g., by narrowing or collimating the light beam.

In some embodiments, a photosensitive semiconductor is fitted around the perimeter of the DOE. In other words, the photosensitive semiconductor is shaped to define an aperture, and the DOE is placed within the aperture. Multiple cathodes and an anode are coupled to the photosensitive semiconductor. Upon the passing of a light beam through the DOE, an internally scattered portion of the light beam, and/or a portion of the light beam that is diffracted with a high order of diffraction, exits from the perimeter of the DOE and hits the photosensitive semiconductor. As a consequence, electric currents flow between the cathodes and the anode.

A detector detects the electric currents, and a processor, in response to the detected electric currents, controls the light source. For example, if abnormal electric currents are detected, the processor may determine that the light beam was not diffracted properly or that the beam power level is too high or too low (relative to a baseline value, which may be established, for example, during calibration). In response thereto, the processor may shut off the light source.

Advantages of embodiments described herein include the following:

(i) In some embodiments, the only portion of the light beam that is used for the testing would not have otherwise been used. In other words, no "useful" portion of the light beam needs to be deflected or attenuated; rather, as noted above, the testing uses only internally scattered light, and/or high-order diffracted light.

(ii) The photosensitive semiconductor, along with the coupled electrodes, can be made relatively small, and the DOE can fit compactly inside the aperture of the semiconductor. In contrast, were other types of testing apparatus—e.g., photodiodes—to be used, the system would be less compact.

System Description

Reference is initially made to FIG. 1, which is a schematic illustration of a system 20 for testing diffraction of a light beam, in accordance with some embodiments described herein.

System 20 comprises a light source, such as a laser 22, which is driven by a laser driver 38 to direct a light beam 24 through a DOE 26, which typically comprises a diffractive lens. DOE 26 comprises a diffractive grating 28, which diffracts light beam 24. Diffractive grating 28 may be disposed on any suitable surface of the DOE, including the surface of the DOE that faces laser 22 (i.e., the front face of the DOE), the opposite surface (i.e., the rear face of the DOE), or, as shown in FIG. 1, an internal surface of the DOE.

FIG. 1 shows a scenario in which the DOE is working properly, such that the angular spread theta (θ) of the light beam is sufficiently greater upon exiting from the DOE than upon entering the DOE. In some cases, however, the diffractive grating may have been damaged, such that the light beam is not sufficiently spread by the DOE. Alternatively or additionally, the intensity of the light beam may be too low, or too high. System 20 identifies such problems, as described in detail below.

Figure 2:
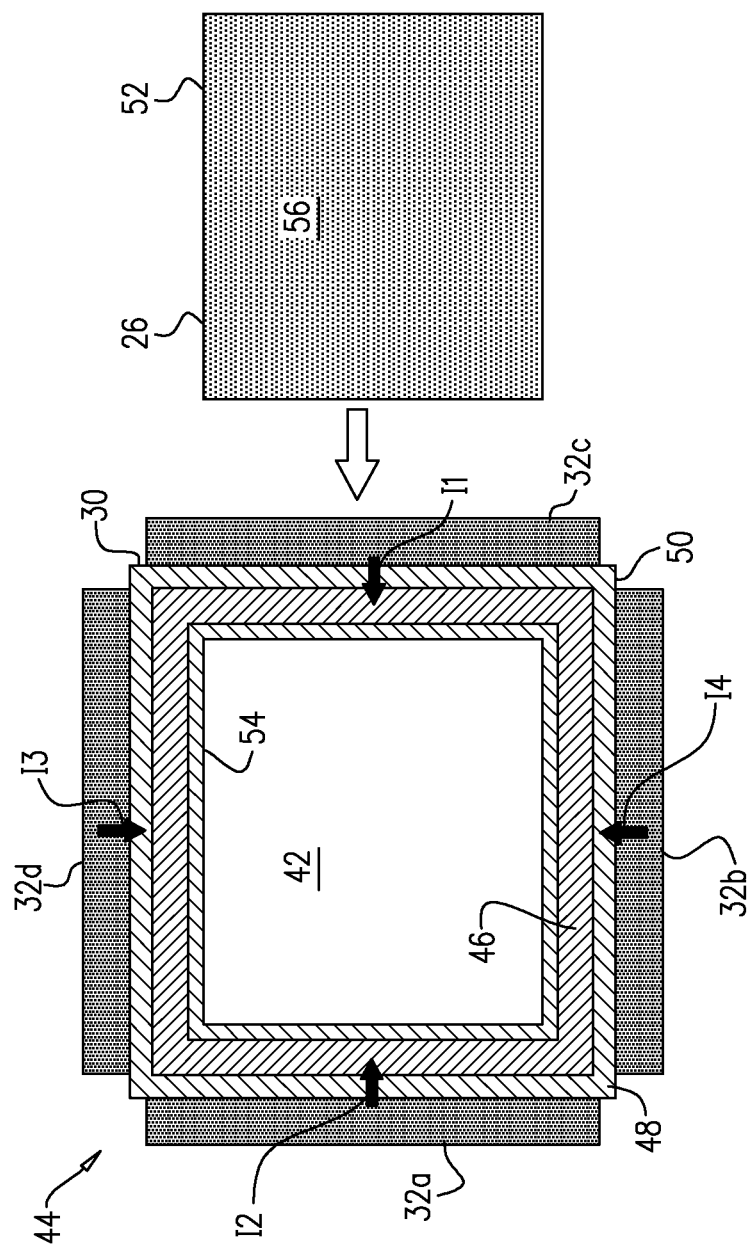

Reference is now made to FIG. 2, which is a schematic illustration of apparatus 44 for testing the diffraction of light beam 24, in accordance with some embodiments described herein. System 20 comprises apparatus 44. (While FIG. 1 shows a cross-sectional side view of apparatus 44, FIG. 2 shows a frontal view of the apparatus.)

Apparatus 44 comprises a photosensitive semiconductor 30, comprising, for example, silicon, and/or any other suitable material. Semiconductor 30 is shaped to define an aperture 42, such as a rectangular (e.g., square-shaped) or circular aperture. In some embodiments, as shown in the figure, the semiconductor is shaped to define a rectangular (e.g., square) front face and a rectangular rear face, and the aperture passes through the semiconductor from the front face to the rear face.

In general, in the context of the present description and claims, the "front face" of the semiconductor is the face of the semiconductor that faces the oncoming light beam, while the "rear face" of the semiconductor is the face that is opposite the front face. Likewise, the "front opening" of the aperture is the opening that faces the light source, while the "rear opening" of the aperture is opposite the front opening. The semiconductor is also shaped to define one or more side faces between the front face of the semiconductor and the rear face of the semiconductor; such side faces include inward-facing side faces 54, which define the perimeter of the aperture, and outward-facing side faces 50. Similarly, the DOE is shaped to define a front face 56 that is placed at the front opening of the aperture, a rear face that is opposite the front face, and side faces 52 that face the inward-facing side faces of the semiconductor. The side faces of the DOE are collectively referred to herein as the perimeter of the DOE.

At least one anode, and a plurality of cathodes, are coupled (e.g., directly attached) to the semiconductor. For example, FIG. 2 shows a single anode 46 coupled to the front face 48 of the semiconductor, and four cathodes 32a, 32b, 32c, and 32d coupled to the semiconductor, each one of the cathodes being coupled to a respective outward-facing side face 50 of the semiconductor.

As indicated by the large left-pointing arrow in FIG. 2, DOE 26 is combined with apparatus 44, by being inserted into aperture 42. Typically, when the DOE is disposed within the aperture, side faces 52 of the DOE are in contact with the perimeter of the aperture, i.e., inward-facing side faces 54 of the semiconductor.

Typically, apparatus 44 is compact, in absolute terms, and/or relative to the size of the DOE. For example, each of the respective perimeters of the faces of the semiconductor is typically less than 80 mm, such as less than 50 mm or 30 mm. In other words, the largest face-perimeter of the semiconductor—which, in the embodiment shown in FIG. 2, is the perimeter of front face 48 (which is typically the same as the perimeter of the rear face)—is typically less than 80 mm, 50 mm, or 30 mm. For example, the size of the front face may be between 5×5 mm and 20×20 mm, such that the perimeter of the front face is between 20 mm and 80 mm. Alternatively or additionally, the ratio of the largest face-perimeter of the semiconductor to the largest face-perimeter of the DOE may be less than nine, such as less than six or three.

In some embodiments, semiconductor 30 comprises a plurality of "one-dimensional" semiconductors that frame aperture 42. For example, instead of cutting out a rectangular aperture from a single rectangular piece of semiconductor material, as suggested by FIG. 2, four strips of semiconductor material may be attached together such as to form a frame that defines a rectangular aperture. For such embodiments, the number of cathodes, and/or the number of anodes, may need to be increased, relative to what is shown in FIG. 2.

Reference is again made to FIG. 1, which shows light beam 24 being directed through DOE 26. Upon the light beam passing through the DOE, and specifically through diffractive grating 28, a portion 40 of the light beam is internally scattered, and/or is diffracted with a relatively high order of diffraction. Part of this light, which may be referred to as "side leakage," exits from the side faces of the DOE. When this light hits the perimeter of the aperture, i.e., the inward-facing side faces of the semiconductor, the conductive properties of the semiconductor change, and consequently, electric currents 58 flow between the cathodes and the anode.

The magnitude of a particular current 58 is an increasing function of the amount of light from the DOE that hits the semiconductor near the cathode from which the current flows. For example, FIG. 1 depicts a larger amount of side-leakage hitting the bottom inward-facing side face of the semiconductor than the top inward-facing side face, and thus, a larger amount of current flowing from cathode 32b than from cathode 32d. FIG. 2 shows a respective arrow for each of the currents. I1 is the magnitude of the current flowing from cathode 32c, I2 is the magnitude of the current flowing from cathode 32a, I3 is the magnitude of the current flowing from cathode 32d, and I4 is the magnitude of the current flowing from cathode 32b.

System 20 further comprises a detector 34, configured to detect electric currents 58. Detector 34 is connected to each of the cathodes, such that the detector measures the respective magnitude of each of the currents. (For simplicity, the connection to only one of the cathodes is shown in FIG. 1.) A processor 36 processes the measured magnitudes, as further described below, and generates an output 60 in response thereto, output 60 typically including control signals to laser driver 38. For example, as further described below, if the electric-current magnitudes indicate that the total amount and/or pattern of side leakage has changed, the processor may shut down the laser, and/or generate an audio or visual output indicative of a problem with the DOE and/or with the laser.

Typically, shortly prior to, or following, the initial assembly of system 20, precise instrumentation is used to establish that the DOE is functioning properly. Subsequently, following the initial assembly of system 20, a calibration procedure is performed, by directing the light beam through the DOE, and measuring the respective magnitudes of the currents caused by side leakage from the DOE. (Typically, even a DOE that is functioning properly is not perfect, and hence, produces some side leakage.) These magnitudes may be used to compute various baseline quantities, to which subsequently computed quantities may be compared, as described below.

Typically, the processor processes the electric-current magnitudes by computing a quantity that is based on one or more of the measured magnitudes, and comparing the quantity to a baseline quantity. For example, the processor may compute the total electric-current magnitude (I1+I2+I3+I4), and compare the total magnitude to the baseline total magnitude (e.g., the total magnitude of current measured during calibration). A change in the total electric-current magnitude, from the baseline total magnitude, may indicate that there is a problem with the DOE and/or with the laser. For example, dirt or scratches on the diffractive grating may be causing the total amount of side leakage, and hence, current, to be greater than the baseline. Conversely, a drastic failure in the DOE, such as an erasure of the diffractive grating, may be causing the total amount of side leakage, and hence, current, to decrease. Alternatively or additionally, the laser may be emitting the light beam with an intensity that is less than or greater than a baseline intensity, thus causing the amount of current to deviate from the baseline.

Alternatively or additionally, the processor computes a quantity that is based on a difference between two of the magnitudes, and/or a ratio between two of the magnitudes, and compares this quantity to a baseline quantity. For example, the quantities $Kx*(I2-I1)/(I2+I1)$ and $Ky*(I4-I3)/(I4+I3)$, where Kx and Ky are scaling factors, may be computed. The first quantity indicates the normalized horizontal bias of the side leakage, while the second quantity indicates the normalized vertical bias of the side leakage. By comparing these quantities to respective baselines, potential problems with the DOE may be identified. In particular, the horizontal bias and/or vertical bias typically indicates the region of the DOE that is defective, which may help identify the source of the problem with the DOE. For example, if the biases indicate that the DOE is defective near the upper-right corner of the DOE, it might be deduced (depending on the circumstances) that a component of the system located near the upper-right corner of the DOE is overheating, thus causing the defect.

It is noted that the scope of embodiments described herein includes comparing any relevant quantity to a baseline, including, for example, any of the individual magnitudes of the currents, or any relevant sum, difference, ratio, or product of the magnitudes.

In some embodiments, the processor simply generates an output in response to ascertaining a deviation from the baseline, without necessarily identifying the cause of the deviation. In other embodiments, the processor further identifies the cause of the deviation; for example, the processor may identify that the diffraction pattern from the DOE is abnormal, or that the power level of the light from the DOE is abnormal. The output from the processor may then include an indication of the identified cause.

In some embodiments, more than one cathode is coupled to each side of the aperture. For example, with reference to FIG. 2, each of cathodes 32b and 32d may be replaced with two cathodes, one cathode covering the left half of the semiconductor, and one cathode covering the right half; alternatively or additionally, each of cathodes 32a and 32c may be replaced with two cathodes, one cathode covering the top half of the semiconductor, and one cathode covering the bottom half. The processor would then use the eight respective currents to more precisely identify the location of the defect in the DOE.

As noted above, the baseline values may be established via a calibration procedure. Alternatively, the baseline values may simply reflect that which is expected of a properly-functioning DOE. For example, I2−I1, and I4−I3, are usually expected to be close to zero; hence, baseline values of zero may be used.

Reference is now made to FIG. 3, which is a schematic illustration of apparatus 44, in accordance with some embodiments described herein. FIG. 3 shows both a side view (left) and a cut-away isometric view (right) of the apparatus.

In FIG. 3, a portion 62 of semiconductor 30 partially covers the rear face of the DOE. Hence, assuming sufficient expansion of the light beam, part of the expanded light beam exits from the rear face of the DOE and hits portion 62 of the semiconductor. The current that is generated as a result of the light hitting portion 62 provides additional information that the processor can use to ascertain whether the laser and DOE are functioning as required. For example, the processor may identify that the light exiting the DOE is insufficiently expanded by identifying a decreased amount of light hitting portion 62.

In the embodiment shown in FIG. 3, semiconductor 30 comprises a layer 63 of material that is separated from the main body of the semiconductor by a layer of insulative material (not shown). Layer 63 comprises portion 62, which partially covers the rear face of the DOE as shown. A separate anode, and one or more separate cathodes, not shown in FIG. 3, are coupled to layer 63, in order to provide separate currents that indicate the amount of light hitting portion 62.

Since portion 62 attenuates part of the light beam, portion 62 typically covers only a relatively small portion of the rear face of the DOE. For example, portion 62 may cover between 10% and 40% of the area of the rear face of the DOE. (For example, if the DOE is 10×10 mm, portion 62 may cover the outer 1 mm along each side of the rear face of the DOE, which is 36% of the area of the rear face.) Such "coverage" is enough to provide information to the processor, yet does not overly attenuate the light beam.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
    a photosensitive semiconductor, shaped to define an aperture;
    at least one anode, and a plurality of cathodes, coupled to the semiconductor;
    an optical element, configured to modify an angular spread of a light beam that traverses the optical element, disposed within the aperture;
    a detector, configured to detect electric currents that pass between the cathodes and the anode in response to a portion of the light beam exiting the optical element and hitting the semiconductor; and
    a processor configured to:
        compute a quantity that is based on respective magnitudes of one or more of the detected electric currents,
        compare the quantity to a baseline quantity, and
        generate an output in response thereto.

2. The apparatus according to claim 1, wherein the optical element is selected from the group consisting of: a diffractive optical element (DOE), and a diffuser.

3. The apparatus according to claim 1, wherein the semiconductor is shaped to define a rectangular front face and a rectangular rear face, the aperture passing through the semiconductor from the front face to the rear face.

4. The apparatus according to claim 3, wherein the semiconductor is further shaped to define four outward-facing side faces between the front face and the rear face, and wherein the cathodes comprise four cathodes, each of which is coupled to a respective one of the outward-facing side faces.

5. The apparatus according to claim 1, wherein a perimeter of the optical element is in contact with a perimeter of the aperture.

6. The apparatus according to claim 1, wherein the processor is further configured to, in response to comparing the quantity to the baseline quantity, identify an abnormal power level of the light beam.

7. The apparatus according to claim 1, wherein the optical element is a diffractive optical element (DOE), and wherein the processor is further configured to, in response to comparing the quantity to the baseline quantity, identify an abnormal diffraction pattern of the DOE.

8. The apparatus according to claim 1, further comprising a light source configured to direct the light beam through the optical element.

9. The apparatus according to claim 8, wherein the output controls the light source.

10. The apparatus according to claim 1, wherein the optical element is shaped to define (i) a front face at a front opening of the aperture, and (ii) a rear face at a rear opening of the aperture, and wherein the semiconductor partially covers the rear face of the optical element.

11. A method, comprising:
    providing a photosensitive semiconductor shaped to define an aperture,
        at least one anode, and a plurality of cathodes, being coupled to the semiconductor, and
        an optical element, configured to modify an angular spread of a light beam that traverses the optical element, being disposed within the aperture;
    detecting electric currents that pass between the cathodes and the anode in response to a portion of the light beam exiting the optical element and hitting the semiconductor;
    computing a quantity that is based on respective magnitudes of one or more of the detected electric currents;
    comparing the quantity to a baseline quantity; and
    generating an output in response to the comparing.

12. The method according to claim 11, wherein the quantity is a total magnitude of the electric currents.

13. The method according to claim 11, wherein the quantity is based on a difference between two of the magnitudes.

14. The method according to claim 11, further comprising, using a light source, directing the light beam through the optical element.

15. The method according to claim 14, wherein the output controls the light source.

16. The method according to claim 11, wherein the optical element is shaped to define (i) a front face at a front opening of the aperture, (ii) a rear face at a rear opening of the aperture, and (iii) one or more side faces, and wherein at least part of the portion of the light beam that hits the semiconductor exits from at least one of the side faces of the optical element.

17. The method according to claim 16, wherein part of the portion of the light beam that hits the semiconductor exits from the rear face of the optical element.

18. The method according to claim 11, wherein the optical element is selected from the group consisting of: a diffractive optical element (DOE), and a diffuser.

19. The method according to claim 11, further comprising, in response to comparing the quantity to the baseline quantity, identifying an abnormal power level of the light beam.

20. The method according to claim 11, wherein the optical element is a diffractive optical element (DOE), and wherein the method further comprises, in response to comparing the quantity to the baseline quantity, identifying an abnormal diffraction pattern of the DOE.

* * * * *